United States Patent
Gilliam

(10) Patent No.: US 7,144,380 B2
(45) Date of Patent: Dec. 5, 2006

(54) TRACTION METHOD AND DEVICE

(76) Inventor: Larry A. Gilliam, 90 Lakeshore La., Chattanooga, TN (US) 37415

( * ) Notice: Subject to any disclaimer, the term of this patent is extended or adjusted under 35 U.S.C. 154(b) by 403 days.

(21) Appl. No.: 10/200,915

(22) Filed: Jul. 23, 2002

(65) Prior Publication Data

US 2003/0018287 A1 Jan. 23, 2003

Related U.S. Application Data

(60) Provisional application No. 60/326,873, filed on Oct. 2, 2001, provisional application No. 60/307,266, filed on Jul. 23, 2001.

(51) Int. Cl.
*A61F 5/00* (2006.01)

(52) U.S. Cl. ........................................ 602/36

(58) Field of Classification Search ............ 602/32–40, 602/17, 5, 18; 482/121, 124, 129, 130
See application file for complete search history.

(56) References Cited

U.S. PATENT DOCUMENTS

| | | | | |
|---|---|---|---|---|
| 1,994,593 A * | 3/1935 | Schmidt | ...................... | 482/72 |
| 2,633,124 A * | 3/1953 | Yellin | .......................... | 602/36 |
| 2,954,026 A * | 9/1960 | Spinks | ......................... | 602/36 |
| 3,105,489 A * | 10/1963 | Zivi | ............................. | 602/32 |
| 3,108,587 A * | 10/1963 | Das | ............................. | 602/36 |
| 3,167,068 A * | 1/1965 | Carr | ........................... | 602/32 |
| 3,168,094 A * | 2/1965 | Siltamaki | .................... | 602/32 |
| 3,601,123 A * | 8/1971 | McFarland | .................... | 602/18 |
| 3,662,750 A * | 5/1972 | Jorgensen | ..................... | 602/35 |
| 3,776,224 A * | 12/1973 | McFarland | .................... | 602/18 |
| 3,835,847 A * | 9/1974 | Smith | .......................... | 602/36 |
| 3,871,366 A * | 3/1975 | Cotrel | ......................... | 602/33 |
| 4,407,274 A * | 10/1983 | Goodley | ..................... | 606/241 |
| 4,580,554 A * | 4/1986 | Goodley | ..................... | 606/201 |
| 4,583,532 A * | 4/1986 | Jones | ........................... | 602/32 |
| 4,827,915 A * | 5/1989 | Gorsen | ........................ | 602/18 |
| 4,865,022 A * | 9/1989 | Gorsen | ........................ | 602/33 |
| 4,869,240 A * | 9/1989 | Boren | ......................... | 602/32 |
| 4,971,043 A * | 11/1990 | Jones | .......................... | 602/36 |
| 5,176,707 A * | 1/1993 | Phillips | ...................... | 606/241 |
| 5,368,281 A * | 11/1994 | Skyba | ......................... | 254/391 |
| 5,401,236 A * | 3/1995 | Summerville | ................ | 602/33 |
| 5,451,202 A * | 9/1995 | Miller et al. | .................. | 602/36 |
| 5,609,566 A * | 3/1997 | Pupovic | ....................... | 601/23 |
| 5,957,876 A * | 9/1999 | D'Amico | ..................... | 602/33 |
| 6,190,345 B1 * | 2/2001 | Henderson | ................... | 602/32 |
| 6,648,844 B1 * | 11/2003 | Kamerman | .................. | 602/36 |

* cited by examiner

*Primary Examiner*—Henry Bennett
*Assistant Examiner*—Huong Q. Pham
(74) *Attorney, Agent, or Firm*—Stephen J. Stark; Miller & Martin PLLC

(57) ABSTRACT

A traction device utilizes a harness connected to the body of a patient, such as the head or hips. The harness is connected by a clip to a tether which passes through a ratchet pulley connected to a first end of a spring chamber. A second end of the spring chamber is connected to a support. As tension is applied to the tether, the ratchet pulley incrementally applies traction to the patient as a first spring housed within the spring chamber deflects with the application of force.

17 Claims, 3 Drawing Sheets

TRACTION METHOD AND DEVICE

This invention claims the benefit of U.S. Provisional Patent Application Nos. 60/326,873 filed Oct. 2, 2001 and 60/307,266 filed Jul. 23, 2001.

BACKGROUND OF THE INVENTION

1. Field of the Invention

This invention relates to a traction method and device, and more particular to a method and device for applying traction to a portion of the spine, either along an upper portion or along a lower portion for cervical or lumbar traction.

2. Prior Art

The spine is made up of vertebrae spaced apart by members commonly known as discs. If these discs become compressed to the point of herniation, they exert pressure on nerves passing between the vertebrae. This can result in a variety of symptoms including neck, shoulder, back and extremity pain, tension, and stress symptom of the neck and the trunk. It is known that traction applied to the spine will, in many cases, stretch out the spine and allow the discs to become de-compressed, somewhat reversing the herniation resulting in alleviation of at least some pain and tension for the user, a highly desirable outcome.

Although a plurality of traction devices are available for various types of therapy, both cervical and pelvic, or lumbar traction, are areas in which an improved device is needed.

A prior art lumbar traction device is illustrated in FIG. 1. The belt is fitted around the patient's waist and has straps which extend from the belt and possibly connected to a spreader bar. The spreader bar, if utilized, or straps is then connected to a device which can be utilized to exert a force on the patient wearing the belt. A number of sources of force have been utilized in the past including weights (both direct application connected to the straps, or utilizing pulleys) and/or forces generated by the body including squatting, or by others pulling against the straps to apply tension to the straps, and thus to the pelvic area.

The prior art devices have a number of shortcomings. Specifically, although some of the attachments to the straps allow for significant application of large forces, there does not appear to be a way to adequately apply measured amounts of forces to the lower back in traction.

FIG. 2 shows a common prior art cervical traction device. The head halter is fitted around the patient's head and connected to a spreader bar. The spreader bar is then connected by a nylon traction cord passing through pulleys to a water bag which may be filled to a desired weight. A wire hanger supports the pulleys from a door. After proper assembly, an upward force is directed along the spine of a person which is substantially equal in magnitude to the weight of the water filled bag.

This prior art device also has a number of disadvantages. Specifically, assembly and disassembly are relatively tedious. The water bag is typically filled and emptied for each use, or otherwise presents the possibility of spilling when stored. A poorly tied knot could result in a sudden and unexpected release of traction from the patient. A dropped water bag could result in a water spill. Futhermore, the redirection of force through pulleys provides a number of locations of possible mechanical failure, or at least, friction which would reduce the desired force applied through traction. Additionally, in order to increase the traction force, the device must be at least partially dissassembled for more water to be added to the water bag.

Accordingly, a need exists to improve over the prior art traction devices.

SUMMARY OF THE INVENTION

Consequently, it is a primary object of the present invention to provide traction to a patient through a traction device in a linear arrangement.

It is a further object of the present invention to provide traction through at least one spring member.

Another object of the present invention is to provide traction through a compact spring arrangement configured to optimally direct forces along the spine of the patient.

Another object of the present invention is to provide a traction method and system which can allow and provide for the incremental increase in traction force to the user.

Accordingly, the present invention provides a traction kit for use in either lumbar or cervical traction. When the lumbar traction embodiment is utilized, the prior art lumbar traction harness is connected to a first end of a spring chamber which may be comprised of one or more compressive spring members configured to compress upon application of a tensile force through the spring chamber. The spring members preferably bottom out upon application of a predetermined traction load to the spring chamber. The second end of the spring chamber may be connected to the end of a patient's bed, or to another appropriate surface.

In operation, the patient places the pelvic harness about the waist, somewhat like putting on a belt, and then connects the pelvic harness to a ratchet pulley which is connected to a spring chamber. The spring chamber is then connected to a support which is fixed to a surface. The patient may then lie down and incrementally apply increasing tension to the spine through the device. It is preferable that the patient lie on his/her back as a safety precaution. If the spring, or springs, bottom out, the patient is made aware of a specific application of traction along the spine. Additionally, the ratchet pulley may make a noise upon each incremental movement. Each noise, or click, will represent a particular traction force applied to the patient.

The cervical traction embodiment utilizes a support to suspend the spring chamber which is connected to a head halter through a rope connected to a ratchet pulley. The rope is pulled until the slack is taken out of the rope. With successive pulling of the rope, the ratchet pulley incrementally applies tension to the spine through the device as the spring chamber is placed under tension.

BRIEF DESCRIPTION OF THE DRAWINGS

The particular features and advantages of the invention as well as other objects will become apparent from the following description taken in connection with the accompanying drawings in which.

DETAILED DESCRIPTION OF THE PREFERRED EMBODIMENT

Figure 1:
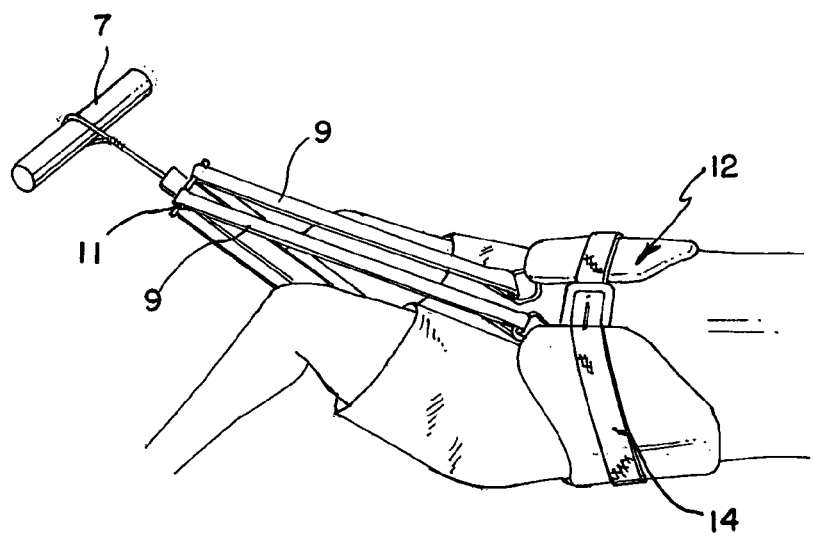
FIG. 1 is a top perspective view of a prior art lumbar traction harness in use.

Referring to FIG. 1, a typical prior art lumbar traction device and its use is illustrated. The device includes a pelvic harness 12 which is available from several vendors. The pelvic harness 12 is placed about the waist of the person and the belt strap(s) 14 connected as illustrated in FIG. 1. Traction straps 9 typically connect the pelvic harness 12 to a force applicator, illustrated as a fixed support 7 in FIG. 1. The patient either pushes away from the force applicator or the force applicator exerts a force on the patient so that traction is applied to the lower portion of the patient's spine.

Figure 3:
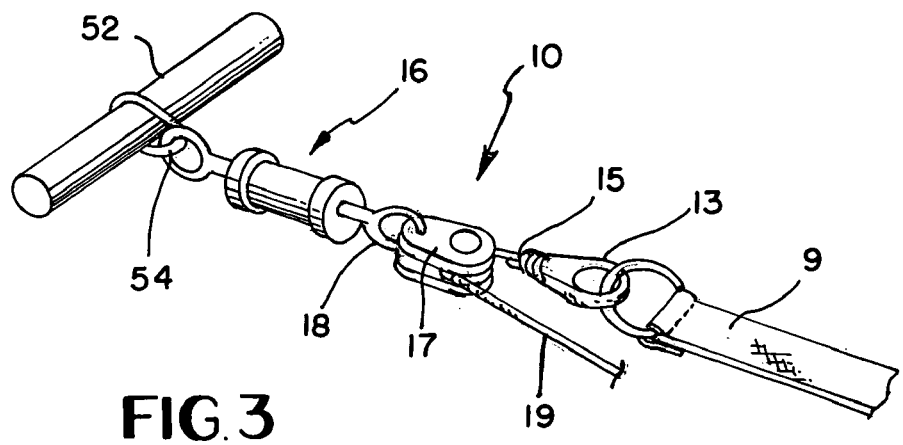
FIG. 3 is a top perspective view of the preferred lumbar traction device.

Instead of connecting the pelvic harness 12 to a spreader bar 11 as is illustrated in FIG. 1, the design disclosed herein connects the traction straps 9 of the pelvic harness 12 to a clip 13 as illustrated in FIG. 3. However a spreader bar could also be utilized, if so desired. The clip 13 may be a carabiner as is often utilized in climbing, or other appropriate connecting device. The clip 13 is then preferably connected via rope 15 to a ratchet pulley 17 which is connected to the first connection point 18 of a spring chamber 16.

Figure 4:
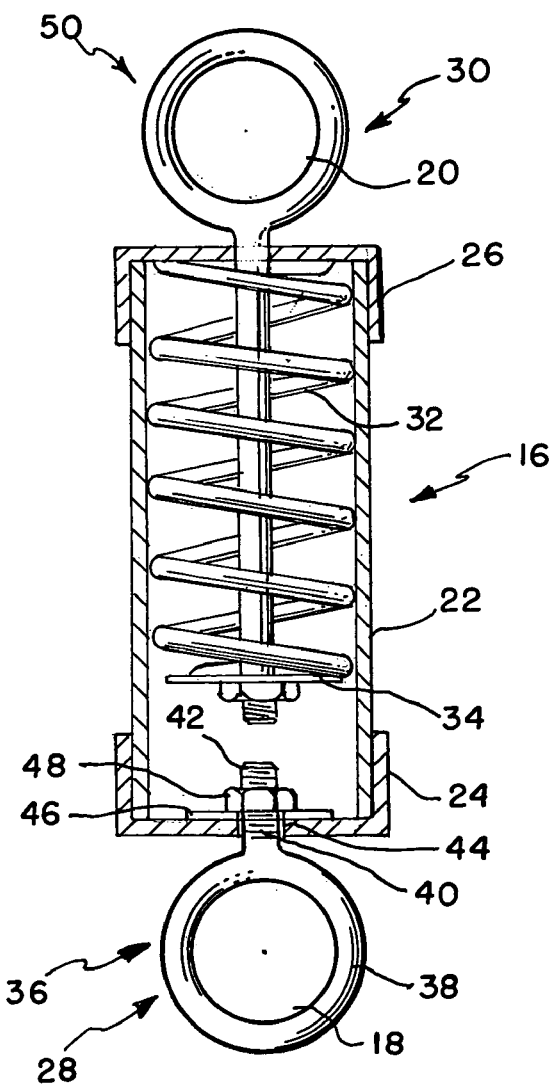
FIG. 4 is a cross sectional view of the spring chamber of FIG. 3.

A first embodiment of a spring chamber 16 is illustrated in FIG. 4 as substantially cylindrical with two opposing connection points 18,20. A segment of PVC (polyvinyl chloride) plumbing pipe of about one inch diameter has been found to form a satisfactory body 22 for the spring chamber. End caps 24,26 are placed on first and second ends 28,30 of the body 22 to contain at least one spring 32 therein. The end caps 24,26 are also preferably PVC plumbing caps. The PVC components are available in the plumbing section of almost any hardware store and are connected together with PVC adhesives.

Figure 2:
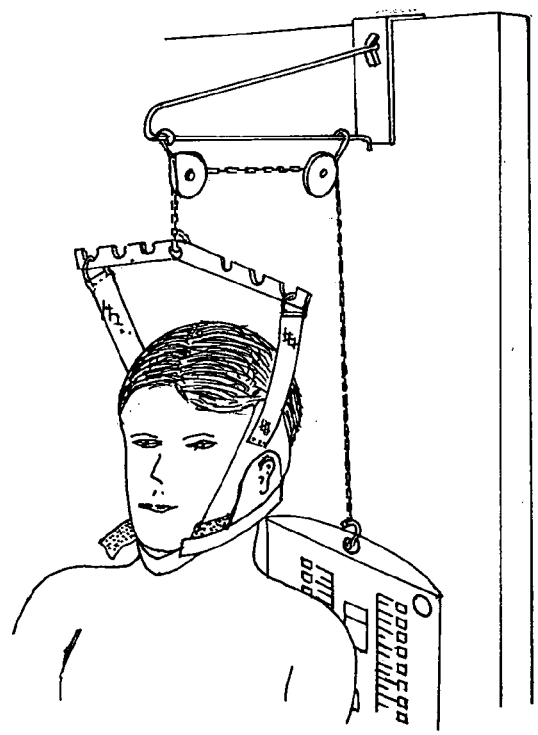
FIG. 2 is a top perspective view of a prior art cervical traction device in use.

The clip 13 is then connected to the first end 28 of a spring chamber 16 as illustrated in FIG. 2. A first eye illustrated in FIG. 3 as the first connection point 18 provides a suitable location to connect the ratchet 17 to the spring chamber 16. The first eye is illustrated as a portion of first eye bolt 36, where the first ring 38 about the first eye connects to a first shaft 40. The first shaft 40 has a threaded portion 42. The first shaft 40 extends through a first opening 44 in the spring chamber 16. The first opening 44 is illustrated as a drilled hole through the first end cap 24.

In order to secure the first eye bolt 36 relative to the spring chamber 16, a first disk 46, or stop, is retained by first nut 48 at the threaded portion 42 of the first eye bolt 36. The first disk 46 retains the first end cap 24 between the first disk 46 and the first ring 38.

The first spring 32 is illustrated in FIG. 4 between the second disk 34 and the second end cap 26. As the first and second eye bolts 36,50 are pulled apart, the first spring 32 compresses. The spring 32 utilized in a prototype was manufactured by the Newcomb Spring Company of Tennessee in Ooltewah, Tenn. The spring 32 preferably is a compression spring which operates substantially linearly over its range of compression to provide the desired traction forces to a user of the traction device 10.

The first spring 32 may be selected so that it bottoms out upon the application of a predetermined force. For pelvic traction applications, it is desirable for the spring 32 to bottom out between about 10 and about 20 pounds, and more preferably at about 36 pounds of pressure. The spring 32 utilized in a preferred embodiment is 4.125 inches long. It has an outer diameter of 0.975 inches and a thickness of 0.1 inches. There are fourteen coils and it travels two inches to completely compress at thinly six pounds of pressure. The stress number is thirty four percent at the low point in the safe range. The majority of the remaining hardware utilized to manufacture the device 10 may be purchased at a hardware store. Of course, the spring chamber 16 could be adapted to utilize a spring in tension by securing one end of the spring to one end of the chamber and the other end to the moveable disk, but it has been found to be preferable to utilize at least one compressive spring 32.

Once a spring chamber 16 is obtained or constructed, the second connection point 20 is connected to a support 52, such as at connection 54. Connection 54 may be a break away joint designed to fail at a predetermined load so that a user may not attempt to utilize the device 10 to cause harm to himself or herself. Alternatively, the connection 54 may be a rope or other suitable retaining mechanism. If a breakaway joint is utilized, it may fail at twenty or more pounds so that an excessive force is not applied by the user. The breakaway joint may be resettable once separated, if so desired.

Another safety aspect of the device 10 is the use of the spring chamber 16 to contain the spring 32 to prevent inadvertent pinching. The spring chamber 16 may be any desired length. About eight inches has been found satisfactory to be functional, as well as sufficiently compact to require relatively small packaging for retail sale.

The preferred method of operation includes placing the pelvic harness 12 about the waist of the individual. The traction straps 9 of the pelvic harness 12 are connected to clip 13. The clip 13 is secured to a rope 15 which passes through a ratchet pulley 17, if utilized, which is connected to the first connection point of the spring chamber 16. The second connection point 20 of the spring chamber is connected to the support 52 at connection 54. After assembling the device 10, the patient then applies traction force by either pulling on the free end 19 of rope 15 and/or by pushing away from the support 52. When the spring 32 bottoms out, the patient is aware of the predetermined maximum applied traction to the spine. Further application of tension may result in the breakaway joint, if utilized, separating or the support 50 failing.

When the ratchet pulley 17 is utilized, it allows the user to somewhat precisely apply traction. The rope 15 may, or may not, initially be taught between the ratchet pulley 17 and the clip 13. When the user desires to apply traction, the free end 19 of the rope 15 is pulled which will take out the slack in the rope 15 between the ratchet pulley 17 and the clip 13. Once the slack is out of the rope 15 between the clip 13 and the ratchet pulley 17, further pulling will cause the spring 32 to apply a force to the user as the rope 15 is incrementally shortened through the operation of the ratchet pulley 17. Each incremental click, or distance, the ratchet pulley 17 moves results in a similar distance the rope 15 is shortened between the first connection point 18 and the clip 13. As the rope 15 shortens, the distance between the connection points 18,20 of the spring chamber 16 increases. Since force equals a spring constant times distance, each incremental distance exerted upon the spring will increase the force of traction exerted on the patient. The clicking noise of the ratchet pulley 17 may be utilized to inform the user of the approximate traction force applied, i.e., one click, one pound of traction, five clicks equals five pounds of traction, etc . . .

The ratchet pulley 17 is available from hardware stores under the trademark ROPE RATCHET (™) and is manufactured by Carolina North Manufacturing, Inc. of Kernersville, N.C. U.S. Pat. No. 5,368,281 is imprinted in the body of the ratchet pulley 17 of the preferred embodiment and is believed to be directed to that device.

The spring 32 is preferably selected so that the clicks of the ratchet 17 correlate with specific traction forces. For lumbar traction the preferred range is between about 8 and about 20 pounds (10–15% of body weight).

The above method and device 10 has been found effective at treating spinal disk herniation, bulging spinal discs, spinal radiculopathy, spondylosis, tension or pain in the back and shoulder muscles, headaches associated with tension, tightness of the neck and/or back, all three grades of whiplash, and/or extremity pain.

Figure 6:
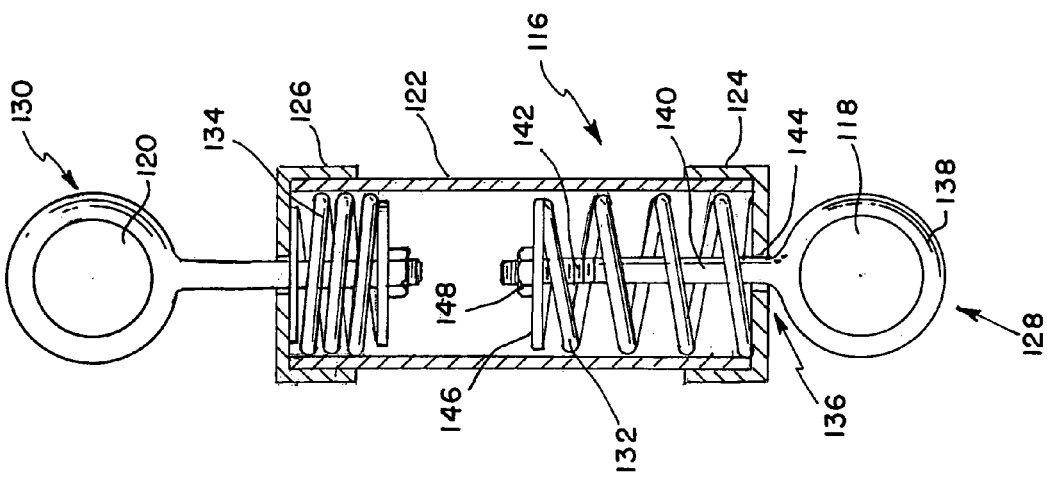
FIG. 6 is a cross sectional view of an alternatively preferred spring chamber.
Figure 5:
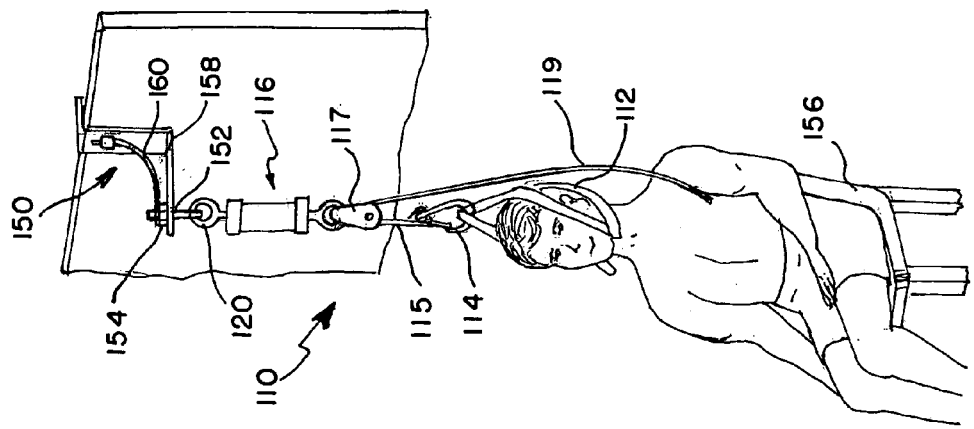
FIG. 5 is a top perspective view of the preferred cervical traction device.

Referring to FIGS. 5 and 6, a cervical traction device 110 and its use is illustrated. The device 110 includes a head halter 112 which is available from several vendors. The head halter 112 is placed over the head of the person and the chin straps connected as illustrated in FIG. 5.

Instead of connecting the head halter 112 to a spreader bar as is illustrated in FIG. 1, it is more preferred to connect the head halter 112 to a clip 114 as illustrated in FIG. 2. However a spreader bar could be utilized, if so desired. The clip 114 may be a carabiner as is often utilized in climbing, or other appropriate connecting device. The clip 114 is then connected via rope 115, or other appropriate tether, to a ratchet pulley 117 which is connected to the first connection point 118 of a spring chamber 116.

The spring chamber 116 is illustrated in FIG. 6 is an alternatively preferred embodiment, but still similar in construction as the embodiment of FIG. 4. The chamber 116 is substantially cylindrical with two opposing connection points 118,120. A segment of PVC (polyvinyl chloride) plumbing pipe of about one inch diameter has been found to form a satisfactory body 122 for the spring chamber. End caps 124,126 are placed on first and second ends 128,130 of the body 122 to contain at least one, and preferably two springs 132,134 therein. The end caps 124,126 are also preferably PVC plumbing caps.

The clip 114 is then connected to the first end 128 of a spring chamber 116 as illustrated in FIG. 5. A first eye illustrated in FIG. 6 as the first connection pont 118 provides a suitable location to connect the clip 112 to the spring chamber 116. The first eye is illustrated as a portion of first eye bolt 136, where the first ring 138 about the first eye connects to a first shaft 140. The first shaft 140 has a threaded portion 142. The first shaft 140 extends through a first opening 144 in the spring chamber 116. The first opening is illustrated as a drilled hole through the first end cap 124.

In order to secure the first eye bolt 136 relative to the spring chamber 116, a first disk 146 is retained by first nut 148 at the threaded portion 142 of the first eye bolt 136. The first disk 146 retains the first spring 132 between the first disk 146 and the first end cap 124. This arrangement allows the first spring 132 to be compressed in a similar manner as the second spring 134 is illustrated as being compressed while retaining the first eye bolt 132 relative to the spring chamber 116.

If a second spring 134 is utilized as illustrated in FIG. 6, it operates similarly to the operation of the first spring 132. The second spring 134 is illustrated as "bottomed out" or fully compressed. The first spring 132 is not bottomed out.

The first and second springs 132, 134 are selected so that they bottom out upon the application of a predetermined force. For traction applications, it is desirable for these two springs to bottom out between about 10 and about 20 pounds, and more preferably at about 15 pounds of pressure. The springs utilized may be compression springs purchased at a hardware store along with the eye bolts 136 and discs 146. Of course, the spring chamber 116 could be adapted to utilize a spring in tension by securing one end of the spring to one end of the chamber and the other end to the moveable disk, but it has been found to be preferable to utilize the compressive springs as first and second springs 132, 134.

Once a spring chamber 116 is obtained or constructed, the second connection point 120 is connected to a support 150, such as at connection 152. Connection 152 may be a break away joint designed to fail at a predetermined load so that a user may not attempt to utilize the device 110 to cause harm to himself or herself. Alternatively, the connection 152 may be an eye bolt retained by a nut 154 or other suitable retaining mechanism. If a breakawayjoint is utilized, it may fail at twenty or more pounds so that an excessive force is not applied by the user. The breakaway joint may be resettable once separated, if so desired.

Another safety precaution illustrated is the use of a chair 156. When sitting in the chair 156, it will be difficult for the patient to exert an inappropriate amount of force to the neck and/or spine through the device 110. The body 122 of the spring chamber 116 may be adjustable or additional links or extenders may be added to the device 110 to accommodate a variety of individuals who have various sitting heights. The support 150 may be constructed of a metal and designed to fail under an excessive load, i.e., if the user exceeds about fifty pounds of force than the holder may give way at bend 158. Safety cord 160 may retain the now failed support 150 to prevent complete collapse, if so desired.

The preferred method of operation includes placing the head halter 112 about the head of the individual. The straps of the head halter 112 are connected to clip 114. The clip 114 is secured to a rope 115 which passes through a ratchet pulley 117, if utilized, which is connected to the first connection point of the spring chamber 116. The second connection point 120 of the spring chamber is connected to the connector 152 of the support which may be hung on a doorway 162 as illustrated in FIG. 2. After assembling the device 110, the patient then eases down, such as into chair 156, and begins to apply tension on the spring chamber 116, such as by pulling on the free end 119 of the rope 115. The first spring 132, or first and second spring 132,134, if utilized, compress under load until bottoming out. When the spring, or springs 132,134 bottom out, the patient is aware of the predetermined applied traction to the neck and/or spine. Further application of tension may result in the breakaway joint, if utilized, separating or the support 150 failing.

When the ratchet pulley 117 is utilized, it allows the user to sit comfortably in the chair 156 prior to applying traction. The rope 115 may, or may not, initially be taught between the ratchet pulley 117 and the clip 114. When the user desires to apply traction, the free end 119 of the rope 115 is pulled which will take out the slack in the rope 115 between the ratchet pulley 117 and the clip 114. Once the slack is out of the rope 115 between the clip 114 and the ratchet pulley 117, further pulling will cause the spring, or springs 132,134 to apply a force to the user as the rope 115 is incrementally shortened through the operation of the ratchet pulley 117. Each incremental click, or distance, the ratchet pulley 117 moves results in a similar distance the rope 115 is shortened between the first connection point 118 and the clip 114. As the rope 115 shortens, the distance between the connection points 118,120 of the spring chamber 116 increases. Since force equals a spring constant times distance, each incremental distance exerted upon the spring will increase the force of traction exerted on the patient. The clicking noise of the ratchet pulley 117 may be utilized to inform the user of the approximate traction force applied, i.e., one click, one pound of traction, five clicks equals five pounds of traction, etc. . . .

The above method and device 110 has been found effective at treating cervical disk herniation, cervical bulging discs, cervical radiculopathy, spondylosis, tension or pain in the upper back and shoulder muscles, headaches associated with tension, tightness of the neck and/or upper back, all three grades of whiplash.

Numerous alternations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A method of incrementally applying traction comprising the steps of:
   providing a spring chamber having a body surrounding a first spring contained therein, said spring chamber connected to a ratcheting pulley operably coupled by a tether to a harness at a first end of the body with said ratcheting pulley located intermediate the harness and the spring chamber; said tether has a free end portion;
   securing a second end of the body, said second end opposite said first end, to a support;
   placing the harness on an appropriate location on a patient;
   removing slack from the tether intermediate the ratcheting pulley and the harness;
   applying tension to the tether, wherein the patient pulls on the free end portion of the tether to incrementally apply traction at a desired location to the patient through the harness with the ratcheting pulley at least assisting in incrementally shortening the tether intermediate the ratcheting pulley and the harness at a distance thereby at least assisting in incrementally increasing tension applied to the patient, and the ratcheting pulley retaining the tether at the distance without continued application of tension to the tether by the patient.

2. The method of claim 1 wherein the step of applying tension provides an audible click with the incremental application of tension.

3. The method of claim 1 wherein the step of applying tension deflects the first spring with the incremental application of traction.

4. The method of claim 1 wherein the step of applying tension compresses the first spring within the body.

5. The method of claim 1 wherein the harness is placed about the head of the patient and the step of applying tension to the rope applies cervical traction to the patient.

6. The method of claim 5 further comprising the step of locating a chair below the patient prior to applying tension to the rope.

7. A traction device comprising:
   a harness;
   a ratcheting pulley operably coupled to the harness by a tether; said tether has s free end portion;
   a spring chamber connected at a first end to the ratching pulley, wherein the ratcheting pulley located intermediate the harness and the spring chamber, said spring chamber having a body with a first spring located therein;
   a support connected to a second end of the spring chamber, said second end opposite the first end, wherein
   application of a force to the spring chamber intermediate the first and second ends alters the length of the first spring, and incremental shortening of the tether intermediate the harness and the ratcheting pulley allows for a patient to incrementally apply a traction force with the spring traction chamber with the patient incrementally shortening the tether intermediate the ratcheting pulley and the harness by pulling the tether on the free end portion of the tether at a location on the tether not intermediate the ratcheting pulley and the harness, and the ratcheting pulley maintaining the force once applied.

8. The traction device of claim 7 wherein the application of the force to the spring chamber compresses the first spring.

9. The traction device of claim 7 further comprising a second spring located within the body.

10. The traction device of claim 7 further comprising a first end cap at a first end of the body with a bore extending therethrough, a shaft extending through the bore, and a stop connected to the shaft within the body with said first spring located intermediate the stop and the first end cap.

11. The traction device of claim 10 wherein the shaft has a connection point external to the body for connecting to one of the ratcheting pulley and the support.

12. The traction device of claim 11 wherein the connection point and shaft are portions of an eye bolt.

13. The traction device of claim 7 wherein the tether is a rope.

14. The traction device of claim 8 wherein the harness is a head harness.

15. The traction device of claim 14 wherein the support has a connector connected to the second end of the spring chamber and is supported by a door.

16. The traction device of claim 15 further comprising a breakaway joint on the support.

17. The traction device of claim 7 further comprising a clip connecting the harness to the tether.

* * * * *